(12) United States Patent
Dayagi et al.

(10) Patent No.: US 7,795,008 B2
(45) Date of Patent: Sep. 14, 2010

(54) SENSITIVE AND SELECTIVE METHOD AND DEVICE FOR THE DETECTION OF TRACE AMOUNTS OF A SUBSTANCE

(75) Inventors: Yohai Y. Dayagi, Rehovot (IL); Lev Dayan, Holon (IL); Moshe Shalom, Herzlia (IL)

(73) Assignee: M.S. Tech Ltd. (IL)

( * ) Notice: Subject to any disclaimer, the term of this patent is extended or adjusted under 35 U.S.C. 154(b) by 538 days.

(21) Appl. No.: 11/643,202

(22) Filed: Dec. 21, 2006

(65) Prior Publication Data

US 2007/0117983 A1 May 24, 2007

Related U.S. Application Data

(60) Division of application No. 10/481,685, filed as application No. PCT/IL02/00492 on Jun. 20, 2002, now Pat. No. 7,159,463, which is a continuation of application No. 09/885,909, filed on Jun. 20, 2001, now Pat. No. 6,526,828.

(30) Foreign Application Priority Data

Jul. 11, 2001 (IL) .................................... 144255

(51) Int. Cl.
C12M 1/34 (2006.01)
G01N 33/553 (2006.01)
C07K 1/10 (2006.01)
C07D 339/04 (2006.01)
C07C 321/02 (2006.01)

(52) U.S. Cl. ...................... 435/287.2; 436/525; 436/80; 530/402; 549/35; 568/25

(58) Field of Classification Search ........................ None
See application file for complete search history.

(56) References Cited

U.S. PATENT DOCUMENTS

| | | | |
|---|---|---|---|
| 3,164,004 A | 1/1965 | King, Jr. | |
| 5,130,257 A | 7/1992 | Baer et al. | |
| 5,177,994 A | 1/1993 | Moriizumi et al. | |
| 5,201,215 A | 4/1993 | Granstaff et al. | |
| 5,245,035 A | 9/1993 | Thomas et al. | |
| 5,283,037 A | 2/1994 | Baer et al. | |
| 5,705,399 A | 1/1998 | Larue | |
| 5,817,921 A | 10/1998 | Tom et al. | |
| 5,852,229 A | 12/1998 | Josse et al. | |
| 6,029,500 A | 2/2000 | Tom | |
| 6,085,576 A | 7/2000 | Sunshine et al. | |
| 6,111,341 A | 8/2000 | Hirama | |
| 6,290,839 B1 | 9/2001 | Kayyem et al. | |
| 6,292,002 B1 | 9/2001 | Pringle et al. | |
| 6,348,795 B2 | 2/2002 | Pringle et al. | |
| 6,526,828 B1 | 3/2003 | Dayan et al. | |
| 6,531,807 B2 | 3/2003 | Tanaka et al. | |
| 6,805,009 B2 | 10/2004 | Burdess et al. | |
| 6,904,786 B2 | 6/2005 | Matsiev et al. | |
| 6,957,565 B2 | 10/2005 | Matsiev et al. | |
| 7,087,148 B1 * | 8/2006 | Blackburn et al. | .......... 205/452 |
| 2002/0180315 A1 | 12/2002 | Tanaka et al. | |
| 2006/0107733 A1 | 5/2006 | Aastrup et al. | |

FOREIGN PATENT DOCUMENTS

| | | |
|---|---|---|
| EP | 992768 | 4/2000 |
| JP | 1244335 | 9/1989 |
| JP | 5187986 | 7/1993 |

OTHER PUBLICATIONS

Wagner et al. Covalent immobilization of native biomolecules onto Au (111) via N-hydroxysuccinimide ester functionalized self-assembled monolayers for scanning probe microscopy. Biophysical Journal 1996, vol. 70. pp. 2052-2066.*

Ferretti et al. Self-assembled monolayers: a versatile tool for the formation of bio-surfaces. Trends in Analytical Chemistry 2000, vol. 19, No. 9, pp. 530-540.*

D.S. Breslow, H. Skolnik, "Multi-Sulfur and Sulfur and Oxygen Five- and Six-Membered Heterocycles", Hercules Research Center, Hercules Incorporated, 1996, pp. 314-347, Interscience Publishers.

Fatibello-Filho, O., Suleiman, A.A., & Gullbaulh, G.G. (1991). "Piezoelectric Crystal Sensor for the Determination of Formaldehyde in Air", Talanta, vol. 38, No. 5, pp. 541-545.

Moritizumi, T., & Nakamoto, T. (Nov. 9-13, 1992). "Odor Sensing System Using Neural Network Pattern Recognition", Signal Processing and Systems Control Intelligent Sensors and Instrumentation; International Conference on Industrial Electronics, Control, Instrumentation, and Automation. vol. 3 of 3, pp. 164501649. San Diego, U.S.A.

Moy, L., & Collins, M. (Feb. 1996). "Electronic Nose and Artificial Neural Networks", American Chemical Society, Anal, Chem., 58, pp. 3077-3084.

Zimmermann, B et al.: "Electrical characterization of high-frequency thickness-shear-mode resonators by impedance and analysis", Sensors and Actuators B, Elsevier Sequoia S.A., Luasanne, CH, vol. 76, No. 103, Jun. 2001, pp. 47-57, XPOO4241093 ISSN: 0925-4005.

Rabe J et al: "Design, manufacturing and characterization of high-frequency thickness-shear mode reasonators" Proceedings IEEE Int. Frequency Control Symposium, Kansas, US2000, XP0105255332.

Auge J et al: "Versatile microcontrolled gas sensor array system using the quartz microbalance principle and pattern recognition methods" Sensors and Actuators B., Elsevier Sequoia S.A., Lausanne, CH, vol. 26, No. 1-3, pp. 181-186, XP004318449 ISSN: 0925-4005.

Tatsuma T et al.: "Multichannel Quartz Crystal Microbalance" Analytical Chemistry, American Chemical Society, Columbus, US, vol. 71, No. 17, Jul. 24, 1999, pp. 3632-3636, XP002229992 ISNN: 003-2700.

(Continued)

*Primary Examiner*—Shafiqul Haq
(74) *Attorney, Agent, or Firm*—Greer, Burns & Crain, Ltd.

(57) ABSTRACT

A piezoelectric crystal element and a sensor utilizing the same are presented for use in a sensor device for identifying at least one foreign material from environment. The crystal element comprises at least one crystal resonator in the form of a inverted mesa structure, which has a membrane-like region and has a certain resonance frequency value. A surface region of the crystal resonator is modified by reactive molecules of a kind capable of interacting with the foreign material to yield a reaction product that effects a change in the resonance frequency of the crystal resonator from said certain resonance frequency value. This change is indicative of the identity and quantity of the foreign material.

4 Claims, 6 Drawing Sheets

OTHER PUBLICATIONS

Abe T et al.: "One-chip multichannel quartz crystal microbalance (QCM) fabricated by Deep RIE" Sensors and Actuators B, Elsevier Sequoia, Lausanne, CH, vol. 82, No. 1-3, May 2000, pp. 139-143, XP004198252 ISSN: 0924-4247.

Zhou X C et al: "Organic Vapour sensors based on quartz crystal microbalance coated with self-assembled monolayers" Sensors and Actuators B, Elsevier Sequoia S.A., Lausanne, CH, vol. 42, No. 1, Jul. 15, 1997, pp. 59-65, XP004094615 ISSN: 0925-4005.

Slater J M et al.: "Gas and Vapour Detection with Poly (Pyrrole) Gas Sensors" Analyst, London, GB, vol. 117, No. 8, Aug. 1, 1992, pp. 1265-1270, XP000604336.

Dabke R B et al: "Electrochemistry of Polyaniline Langmuir-Blodgett Films", Thin Solid Films Sensors and Actuators B, Elsevier Sequoia S.A., Lausanne, CH. vol. 335, No. 1-2, Nov. 19, 1998, pp. 203-208, XP004153005 ISSN: 0040-6090.

Kim S-R et al: "Preparation of Polythiophene LB films and their gas sensitivities by the Quartz Crystal Microbalance" International Conference of Science and Technology of Synethetic Metals (ICSM '94), Seoul, South Korea, Jul. 24-29, 1994, vol. 71, No. 1-3, pp. 2027-2028, XP002229993 Synthetic Metals, Apr. 1, 1995, Switzerland, ISSN: 0379-6779.

Cygan M T et al: Calixarene monolayers as quartz crystal microbalance sensing elements in aqueous solution, Analytical Chemistry, American Chemical Society. Columbus, US, vol. 71, No. 1, 1999, pp. 142-148, XP000799230 ISSN: 0003-2700.

Paolesse R et al: "Self-assembled monolayers of mercaptoporphyrins as sensing material for quartz microbalance chemical sensors", Sensors and actuators B, Elsevier Sequoia, S.A., Lausanne, CH, vol. 47, No. 1-3, Apr. 30, 1998, XP004147320 pp. 70-76, ISSN: 0925-4005.

Carrara M. et al: "Carboxylic acid anchoring groups for the construction of self-assembled monolayers on organic electrodes,", Synth Met: Synthetic Metals, vol. 121, No. 1-3, pp. 1633-1634, Mar. 15, 2001, XP001151655.

Michalitsch R. et al: "Self-assembled monolayers based on alpha-functionalized quaterthiophene" Proceedings of the 1999 international Conference on science and Technology of Synthetic Metals (ICSM-98), Montpellier, vol. 102, No. 103 part 2, Jul. 12, 1998, p. 1319, XP002239417.

Becker H.J., Tamsma A.F, Rec. Trav. Chim, 1938, 1938, p. 1183-1210 (English abstract enclosed).

Nakao H. et al. Biosci. Biotech. Biochem.60(4) 1996, p. 683-684.

* cited by examiner

SENSITIVE AND SELECTIVE METHOD AND DEVICE FOR THE DETECTION OF TRACE AMOUNTS OF A SUBSTANCE

This is a divisional of application Ser. No. 10/481,685, filed Mar. 17, 2004, now U.S. Pat. No. 7,159,463 which is a 371 of PCT/IL02/00492, filed Jun. 20, 2002, which is a Continuation of application Ser. No. 09/885,909, filed Jun. 20, 2001, now U.S. Pat. No. 6,526,828, issued Mar. 4, 2003.

FIELD OF THE INVENTION

This invention is in the field of mass detection using a coated piezoelectric sensor.

BACKGROUND OF THE INVENTION

In recent years there has been a growing interest in coated piezoelectric crystals, not only as highly sensitive and selective detector of various air pollutants but also as simple, inexpensive and portable device. The high sensitivity and simple relationship between mass and frequency make the quartz crystal microbalance as an ideal tool for the study of adsorption and as a selective chemical sensor in many applications.

The principle of the detection is that the frequency of vibration of an oscillating crystal is decreased by the adsorption of a foreign material on its surface. A gaseous pollutant is selectively adsorbed by a coating on the crystal surface, thereby increasing the weight of the crystal and decreasing the frequency of vibration. The decrease in the frequency is proportional to the increase in weight due to the presence of gas adsorbed on the coating according to the following equation: $\Delta F = K \cdot \Delta C$. Here, $\Delta F$ is the frequency change (Hz), K is a constant which refers to the basic frequency of the quartz plate, area coated, and a factor to convert the weight of injected gas (g) into concentration (ppm), and $\Delta C$ is concentration ppm) of sample gas.

U.S. Pat. No. 3,164,004 teaches that a piezoelectric quartz crystal coated with a substrate selectively sensitive to changes in the atmospheric environment can serve as a detection device in fluid analyzers. In general, this discovery is based on the principle that the oscillation of a crystal, both in frequency and amplitude, is in part a function of its weight. The change in weight of a crystal coated with a substrate selectively sensitive to a particular contaminant when placed in an environment containing that contaminant is, in turn, at least partly a function of the concentration of the contaminant. Therefore, the measurement of the change in oscillation characteristics of a coated crystal sensitive to a particular contaminant upon exposure to a given atmosphere is a direct and highly sensitive measure of the presence and concentration of that contaminant. Variations of and improvements in this basic method are shown, inter alia, in the following publications U.S. Pat. No. 5,177,994; U.S. Pat. No. 5,817,921, and U.S. Pat. No. 6,085,576; Japanese Patents Nos. 1244335, and 5187986; European Patent No. 992768, and "*Electronic Nose and Artificial neural Networks*", L. Moy and M. Collins, American Chemical Society, Anal. Chem., 1986, 58, pp. 3077-3084; "*Piezoelectric Crystal Sensor for the Determination of Formaldehyde in Air*", Talanta, Vol. 38, No. 5, pp. 541-545, 1991; "*Odor Sensing System Using Neural Network Pattern Recognition*", Toyosaka Moriiznmi and Takamichi Nakamoto, International Conference on Industrial Electronics, Control, Instrumentation and Automation, Nov. 9-13, 1992, Marriot Mission Valley, San Diego, USA.

A sensor has two equally important requirements: sensitivity and selectivity. There are two ways of achieving high selectivity and specificity towards xenobiotic (non-self) agents as we can learn from nature: (i) the immune system, in which a unique sensor (i.e. antibody) is being synthesized for any invader (i.e. antigen). This is a very complicated mechanism that involves a spontaneous constant synthesis of new molecules that are examined to fit the antigen; (ii) the olfactory system, in which a huge array of receptors are located in the nose in such a way that a molecule entering the nose interacts with some of the receptors; the brain then translates the pattern of the signals to an odor. In this case the odor can be a single molecule or a composition of several different molecules.

The combination of a number of sensors and a pattern recognition routine is known as an "electronic nose". Using the combination of chemical sensors, which produce a fingerprint of the vapor or gas, the recognition algorithms can identify and/or quantify the analytes of interest. The electronic nose is capable of recognizing unknown chemical analytes, odors, and vapors. In practice, an electronic nose is presented with a substance such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

A wide variety of commercial applications are available for electronic noses including, but not limited to, detection of explosives or drugs, environmental toxicology, biomedicine, such as microorganism classification or detection, material quality control, food and agricultural product monitoring, ambient air monitoring, employee protection, emissions control, and product quality testing. Referring to the detection of explosives, a number of laboratory techniques for the detection of explosives are known, using gas chromatography, mass spectrometry, ion mobility spectroscopy, NMR, plasma chromatography and visible chromatography. While some of these techniques are capable of ppb detection, the detection systems need elaborate techniques for operation, are usually not portable and simple, and are thus not useful for field use.

SUMMARY OF THE INVENTION

There is a need in the art for a sensing device that is compact, capable of detecting trace amounts of mass of $10^{-15}$ g order and even less, that is useful in a broad variety of applications and can respond accurately to a broad variety of gases, analytes, odors and fluids.

The present invention provides a sensing device (also referred to as an electronic-nose device) that is compact and, in certain embodiments, configured to be a handheld device. The device can be used to measure or identify one or more analytes in a medium such as vapor, liquid or gas.

The main idea of the present invention is based on the use of a piezoelectric crystal element (such as quartz, ceramics), which, on the one hand, can be manufactured by the existing techniques to be mountable in a sensor device, and, on the other hand, has a sufficiently thin (membrane-like) region, which defines a sensing region of the crystal element, thereby providing increased sensitivity as compared to the known sensors.

The crystal element, according to the present invention, is in the form of the so-called "inverted mesa structure", in which a relatively thin membrane-like region (resonator) is surrounded by relatively thick end regions of the crystal element. A pair of electrodes are located on the opposite sides of this membrane-like region. The electrodes and/or the membrane-like region have a surface region coated with reactive molecules, thereby presenting a sensing region of the device electrically excitable by the environment (which can be gas or liquid). The reactive coating molecules interact with a foreign material from the environment to yield a reaction product that effects a change in the resonance frequency of the crystal resonator from a certain resonance frequency value characterizing said crystal resonator.

The reactive coating molecules are preferably organized in a self-assembled monolayer (SAM) formed on the surface of the electrodes and/or the membrane-like region (i.e. on the surface of a substrate). The monolayer consists of receptor compounds comprising a linker that connects said compound to the surface of said substrate, an optional spacer, a structural element and an active head group.

There is thus provided according to one aspect of the present invention, a piezoelectric crystal element for use in a sensor device for identifying at least one foreign material from environment, the crystal element comprising at least one crystal resonator in the form of an inverted mesa structure having a membrane-like region, which is substantially thinner as compared to end portion of the crystal resonator surrounding said membrane-like region and has a certain resonance frequency value, a surface region of said at least one crystal resonator being modified by reactive molecules of a kind capable of interacting with said at least one foreign material to yield a reaction product that effects a change in the resonance frequency of said membrane-like region from said certain resonance frequency value, said change being indicative of the identity and quantity of said at least one foreign material.

According to another aspect of the present invention, there is provided a piezoelectric sensor for use in a device for identifying at least one foreign material from environment, the sensor comprising a piezoelectric crystal element having at least one crystal resonator in the form of an inverted mesa structure defining a sensing membrane-like region which is substantially thinner as compared to end portion of the crystal resonator surrounding said membrane-like region and has a certain resonance frequency value, and electrodes formed on opposite sides of said sensing membrane-like region, said at least one crystal resonator having a surface region modified with molecules capable of interacting with at least one foreign material from the environment to which the crystal resonator is exposed to yield a reaction product that effects a change in the resonance frequency of said membrane-like region from said certain resonance frequency value, said change being indicative of the identity and quantity of said foreign material.

The input and output of the sensor is connectable to a control means operable for actuating the at least one crystal resonator and measuring the change in the resonance frequency, to generate measured data representative of the identity and quantity of said foreign material.

The metal electrodes used in the sensor may comprise a metal selected from Au, Pt and Al, with Au being the most preferred metal. The modified surface region may include the surface of the membrane region, the surface of the respective electrode, or both.

The control means comprises an actuator utility (either a common oscillator for all the crystal resonators or a plurality of oscillators each associated with a corresponding one of crystal resonators, and one or more switches depending on the number of crystal resonators) and a detector utility. The actuator utility actuates said at least one crystal resonator to put it in operation. The detector utility comprises an electronic circuit for detecting the frequency of the at least one crystal resonator to enable measurement of said change.

According to yet another aspect of the present invention, there is provided a piezoelectric sensor device for identifying at least one foreign material from environment, the device comprising:

(i) a sensor including a piezoelectric crystal element having at least one piezoelectric crystal resonator in the form of an inverted mesa structure defining a sensing membrane-like region, which is substantially thinner as compared to end portion of the crystal resonator surrounding said membrane-like region and has a certain resonance frequency value, and having electrodes formed on opposite sides of said sensing membrane-like region, said at least one crystal resonator having a surface region modified with molecules capable of interacting with a foreign material of the environment to yield a reaction product that effects a change in the resonance frequency of said at least one membrane-like region from said certain resonance frequency value, said change being indicative of the identity and quantity of said foreign material; and (ii) a control means operable for actuating said at least one crystal resonator, measuring the change in the resonance frequency, and generating measured data representative of the identity and quantity of said foreign material.

Preferably, the crystal element comprises an array of spaced-apart crystal resonators, each in the form of the inverted mesa structure formed with a pair of electrodes at opposite surfaces of the membrane-like region, thereby defining an array of sensing regions affectable by the environment. The surface regions of different crystal resonators are modified with different reactive molecules, thereby enabling the detection of various foreign materials contained in the environment. Au electrodes, for example, are suitable for modification with sulfur containing molecules. When the quartz membrane region participates in the sensing operation, then the quartz may be modified by different functional groups, such as, for example, silanes.

The crystal element may comprise the so-called "reference" or "passive" crystal resonator (without coating) which is screened from the environment. The change of the resonance frequency of the "active" crystal resonator caused by the foreign material is thus determined as a difference between the resonance frequencies of the active and passive elements. Alternatively, such reference data (or the certain value of the resonance frequency characterizing the crystal resonator) may be stored in a memory of the control means.

Preferably, the crystal resonators are equally distanced from the actuator utility (oscillator). This may be implemented by arranging the resonators (wherein one of the crystal resonators may be the reference or passive element) in spaced-apart relationship along a circular path and placing the common oscillator either in the center of the circle or at any other location at the central axis of the circle. Thus, the crystal element may comprise a disc carrying the circular array of the equally spaced piezoelectric crystal resonators, and the actuator utility located on the central axis of the disc. It should be understood that the entire disc may be made of a piezoelectric crystal in which case the crystal is patterned to define the circular array of spaced-apart inverted mesa structures (i.e., the circular array of membrane-like regions defining the sensing regions). In another examples of the invention, the plurality of oscillators are placed on the disc carrying the plurality of crystal resonators, and all the crystal resonators are equally distanced from their respective oscillators.

According to yet another aspect of the present invention, there is provided a piezoelectric sensor device for identifying at least one foreign material from environment, the sensor device comprising:

an array of spaced-apart crystal resonators, each crystal resonator being in the form of an inverted mesa structure having a membrane-like region, which is substantially thinner as compared to end portion of the crystal resonator surrounding said membrane-like region and has a certain resonance frequency value, each of the crystal resonators being excitable by the environment to cause a change in the resonance frequency thereof from said certain resonance frequency value; and an actuator utility for operating the crystal resonators, said actuator utility being arranged such that each of the crystal resonators is spaced the same distance from its associated oscillator of the actuator utility.

The modification of the surface region of the crystal resonator may be achieved by two alternative techniques: (1) construction of organized, self assembled monolayers (SAM); or (2) formation of polymeric layer.

The organized, self-assembled monolayer (SAM) consists of receptor compound comprising a linker that connects said compound to the surface of said substrate, an optional spacer, a structural element and an active head group.

Relating to the formation of a polymeric layer, the preferred technology for forming a polymer layer in a controlled manner is by electropolymerization.

It should be noted that the device of the present invention could be used in gaseous medium, liquid medium or a combination thereof, thus acting as an electronic nose and/or as an electronic tongue. An electronic tongue is a device similar to the electronic nose, but capable of operating in a liquid medium, and enables the analysis of solutes in a solution. Such a combined device provides for simultaneous analysis of a solution and it's vapors, providing a complete picture of the detected material.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
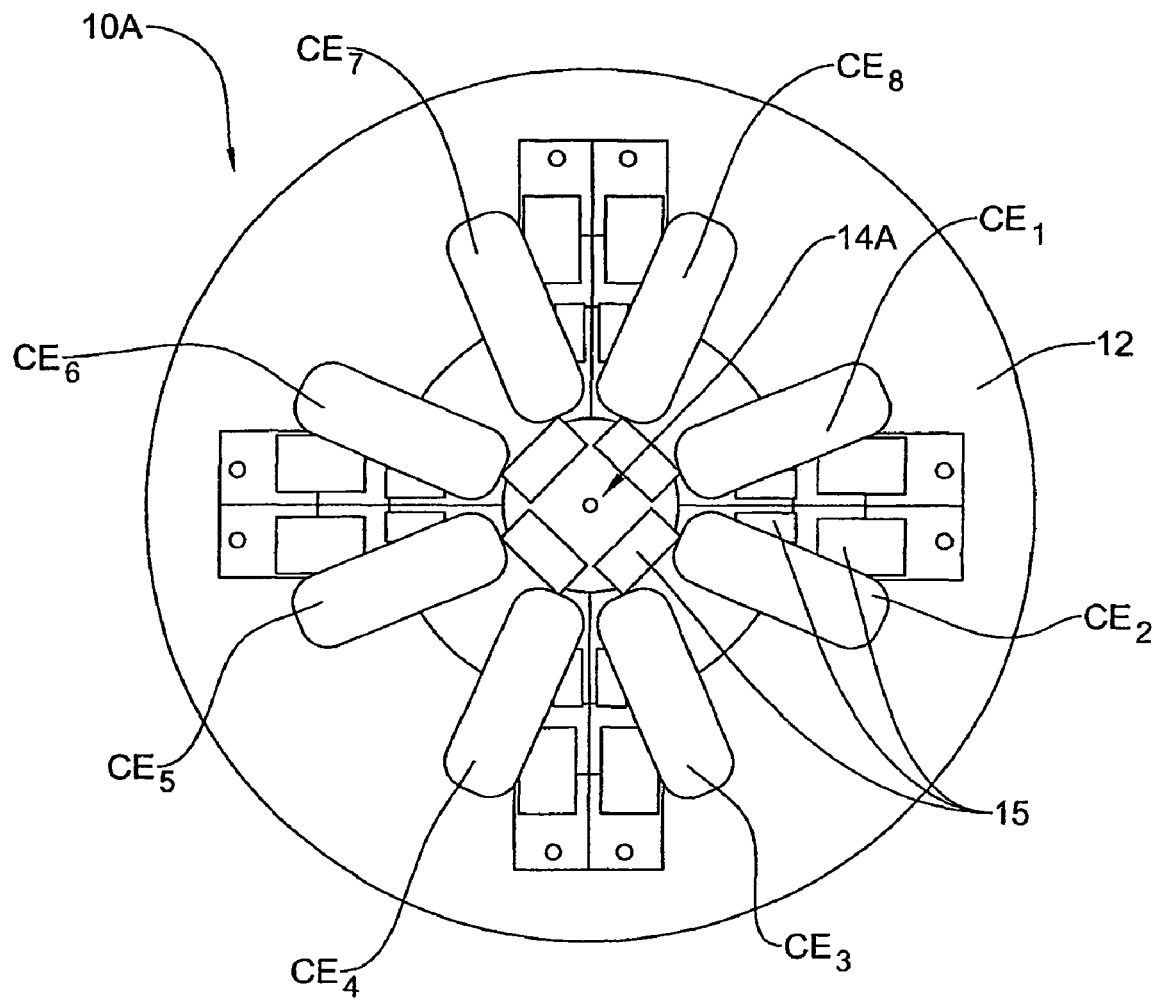
FIGS. 1A and 1B are schematic illustrations of two examples of a sensor device according to the invention.

Referring to FIG. 1A, there is illustrated a sensor device 10A according to the invention, which, in the present example, is implemented as a disc-shaped printed circuit board 12. The device 10 comprises such main constructional parts as sensor comprising a piezoelectric crystal element (quartz crystal in the present example), and a control means.

The crystal element may comprise one or more crystal resonators, eight such resonators $CE_1$-$CE_8$ made of quartz crystal being shown in the present example. The control means comprises electronic components, which are incorporated in the disc 12 and include an actuator utility 14A, and a detector utility, generally at 15. The actuator utility 14A is composed of an oscillator, and a plurality of switches associated with the crystal resonators, respectively, as will be described more specifically further below with reference to FIG. 4A.

The quartz crystal resonators $CE_1$-$CE_8$ are arranged in a spaced-apart relationship along a circular path centered around the actuator utility 14A. This arrangement equally distances all the quartz crystal resonators from the oscillator. It should be understood that the same can be achieved by placing the oscillator at any location on the central axis of the circle formed by the array of equally spaced quartz crystal resonators.

It should be noted, although not specifically shown, that one of the crystal resonators may be a reference one screened from the environment, to which the other "active" resonators are exposed. The provision of such a reference crystal resonator is optional, and may be replaced by the storage of a reference signal in a memory of the control means.

Figure 1B:
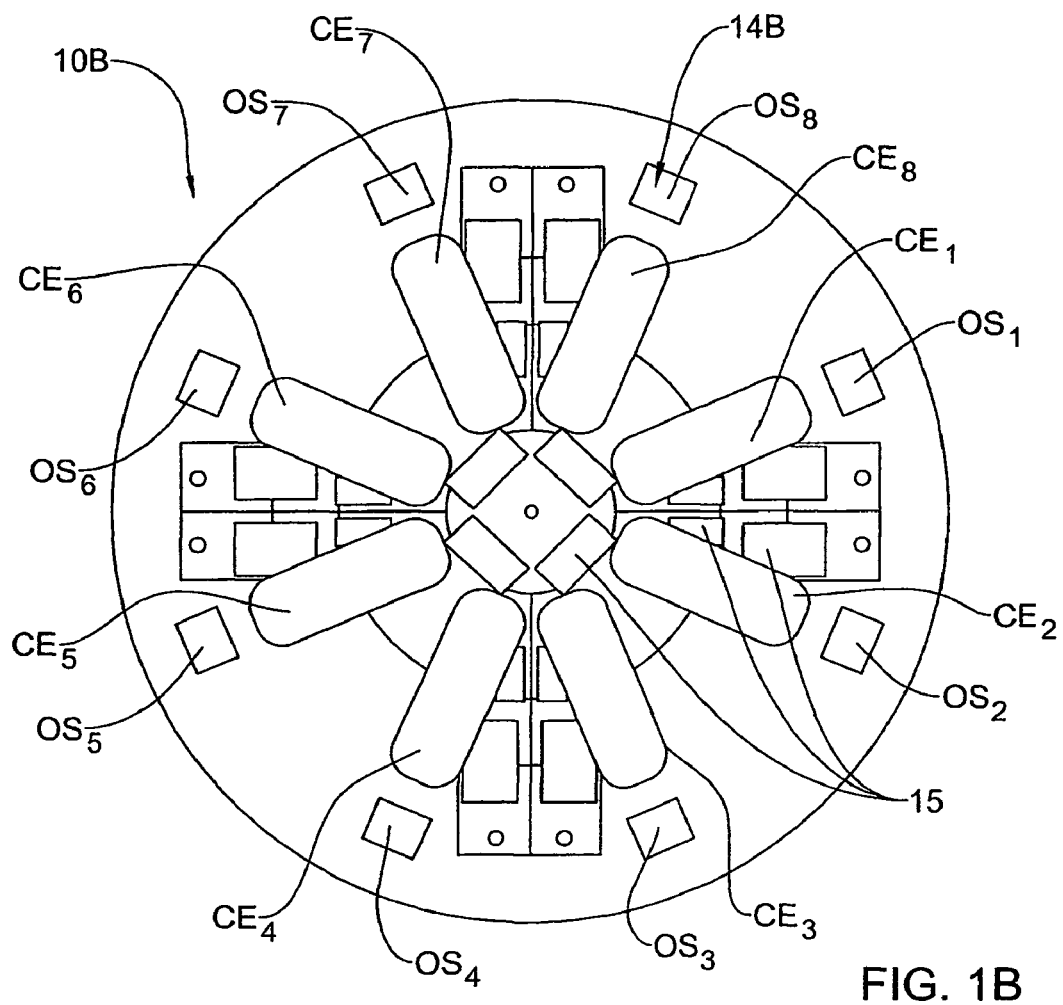

FIG. 1B exemplifies a sensor device 10B according to the invention. To facilitate understanding, the same reference numbers are used to identify the common components in the devices 10A and 10B. The device 10B thus differs from the device 10A in the construction of an actuator utility 14B, which utilizes several oscillators—eight oscillators $OS_1$-$OS_8$ in the present example each associated with a corresponding one of eight crystal resonators $CE_1$-$CE_8$. Separate operation of each crystal resonator by its associated oscillator allows for increasing the number of crystal resonators in the matrix (practically with no limitations for the number of crystal resonators). Here, similar to the device 10A, the symmetry of accommodation of the crystal resonators is maintained, i.e., each of the crystal resonators is spaced the same distance from the respective oscillator.

Figures 2A, 2B, 2C:
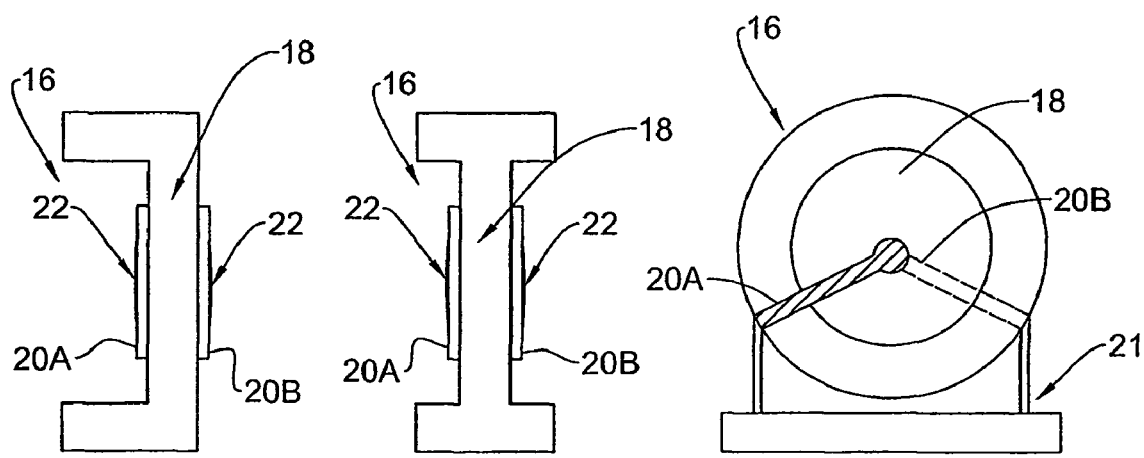
FIGS. 2A to 2C more specifically illustrate a crystal resonator in a piezoelectric crystal element of the device of either of FIGS. 1A and 1B.

Turning now to FIGS. 2A-2C, each of the quartz crystal resonators is an inverted mesa structure 16 defining a membrane-like region 18 having a thickness of about several micrometers. To fabricate such an inverted mesa structure, a crystal is patterned either at one side thereof to form one recess (FIG. 2A), or at both opposite sides thereof to form two opposite recesses (FIG. 2B), thereby forming the membrane central region 18 of a sufficiently small thickness (to obtain desirably high sensitivity of the sensor device) between two relatively thicker end portions of the structure surrounding the membrane-like region. Metal electrodes 20A and 20B (made from Al, Pt or Au) are deposited onto opposite surfaces of the membrane-like region 18. As shown in the example of FIG. 2C (illustrating a crystal element with a single resonator), the crystal element is supported by a holder 21. Preferably, Au-based glue is used for attaching the crystal element to the holder.

The active quartz crystal resonator is formed with a surface region 22 (exposed to the environment) modified by reacting molecules intended to interact with one or more specific foreign materials that may be present in the environment. In the present example, this is implemented by coating the electrodes 20A and 20B with such a molecule, as will be described more specifically further below. It should, however, be noted that, generally, such a modified surface region may include the surface of the electrodes (or only one electrode located on that side of the device by which it is exposed to environment), the surface of the membrane-like region, or both. An interaction between these molecules and one or more specific foreign material affects the frequency of vibration of the crystal resonator to change from the certain resonance frequency value. This change is detected by the corresponding electronic component of the control means.

As indicated above, the principle of the detection is that the frequency of vibration of an oscillating crystal is decreased by the adsorption of a foreign material on its surface. A foreign material, for example a gaseous pollutant, is selectively adsorbed by the coating (on the crystal surface or/and on the metal electrode surface coating the crystal surface), thereby increasing the weight of the crystal and decreasing the frequency of vibration. The decrease in the frequency $\Delta F$ (Hz) of the crystal resonator is proportional to the increase in its weight due to the presence of foreign material absorbed on the coating and is represented by the following equation: $\Delta F = K \cdot \Delta m$, where $\Delta m$ is the change in mass per unit surface area and $K$ is a constant which refers to the basic frequency of the piezoelectric crystal plate.

Figure 3A:
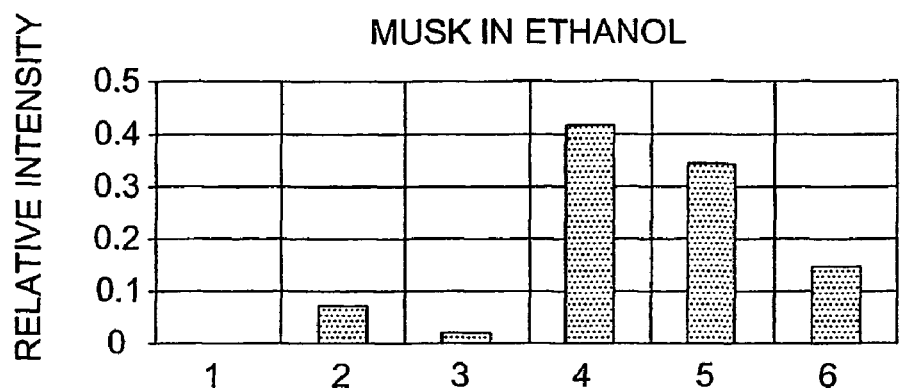
FIGS. 3A to 3C illustrate experimental results of the absorption of three different analytes: musk in ethanol, TATP and TNT.
Figure 3B:
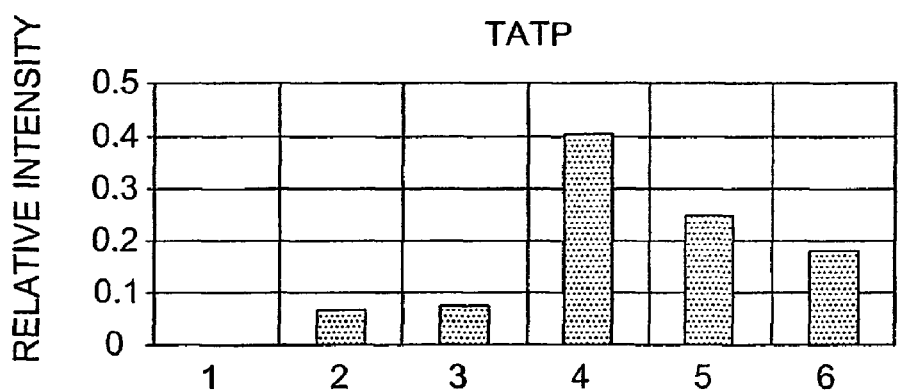
Figure 3C:
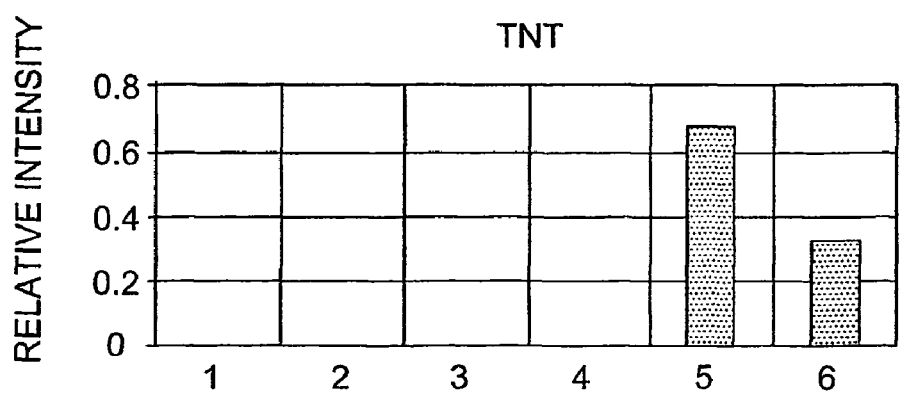

It should be understood that what is actually detected by the device of the present invention utilizing several crystal resonators is the so-called "electronic image" or pattern of the intensities and shape of response of each of the crystal resonators in the crystal element. These responses are indicative of the decay of the vibrating frequencies of the crystal resonators caused by the absorption of foreign materials. FIGS. 3A to 3C illustrate experimental results in the form of three different measured patterns (electronic images), respectively, of the absorption of three different analytes: musk oil in ethanol, TATP and TNT.

Figure 4A:
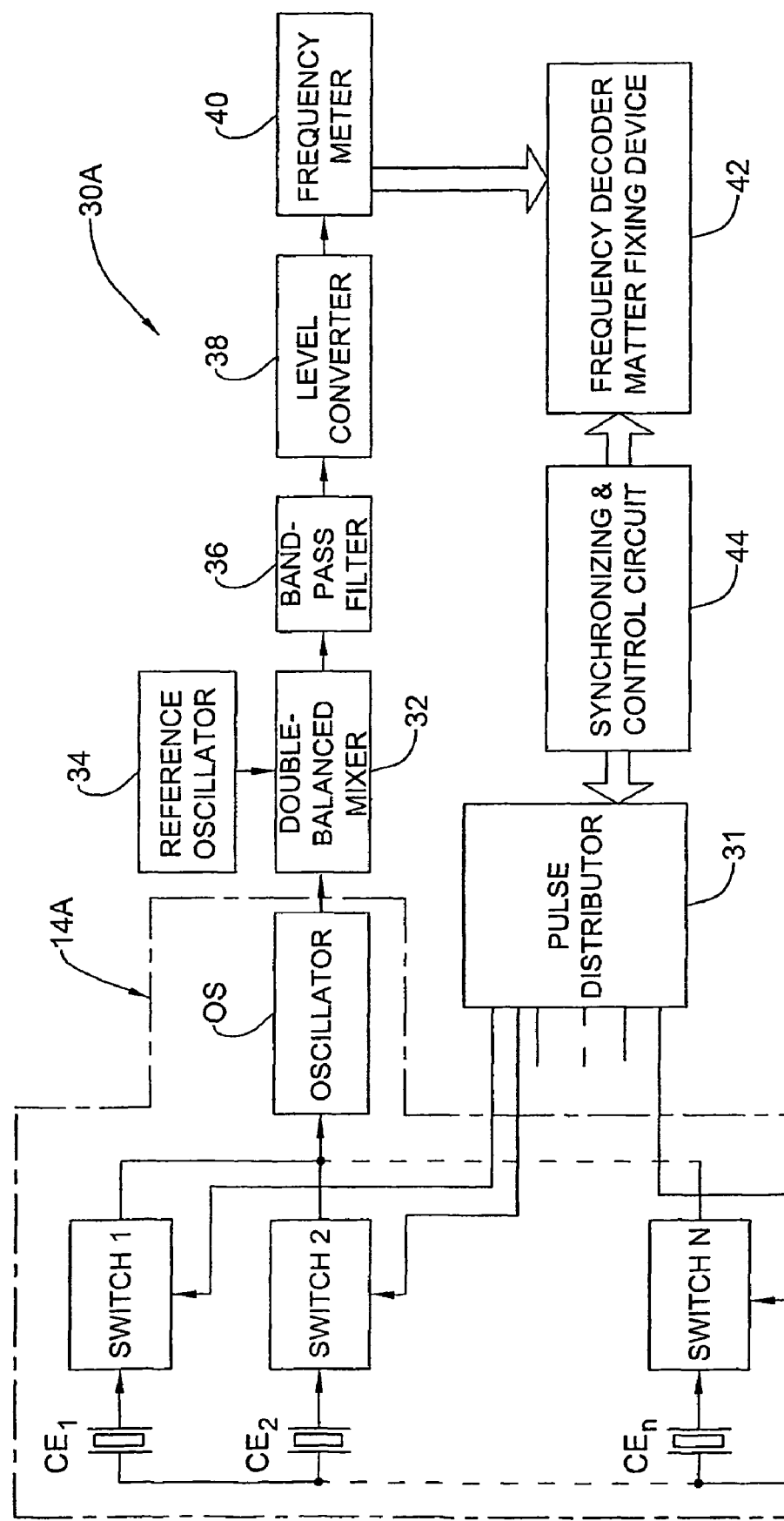
FIGS. 4A and 4B are block diagrams of the devices of FIGS. 1A and 1B, respectively, showing more specifically a control means of the device.

FIG. 4A illustrates a block diagram of the sensor device 10A, showing the main components of the control means 30A for operating and processing the response of (n−1) active quartz crystal resonators $CE_2$-$CE_n$ utilizing a reference (passive) quartz crystal resonator $CE_1$. The actuator utility 14A of the control means 30A comprises n switches, which, by n input ports thereof, are connected to the n quartz crystal resonators $CE_1$-$CE_n$, respectively, and by the output ports thereof, are connected to the input port of an oscillator OS. The switches, by other input ports thereof, are connected to a pulse distributor 31. The oscillator's output is connected to one input port of a double balanced mixer 32, the other input port of the mixer 32 being connected to the output port of a reference oscillator 34. The output port of the double balanced mixer 32 is connected to the input of a band-pass filter 36, whose output port is connected to the input of a level converter 38, which, in turn, is connected by its output port to the input of a frequency meter 40. All the outputs of the frequency meter 40 are connected to the respective inputs of a frequency decoder matter fixing device 42. The other input ports of the device 42 are connected to corresponding output ports of a synchronizing and control circuit 44, whose output ports are connected to the inputs of the pulse distributor 31.

Figure 4B:
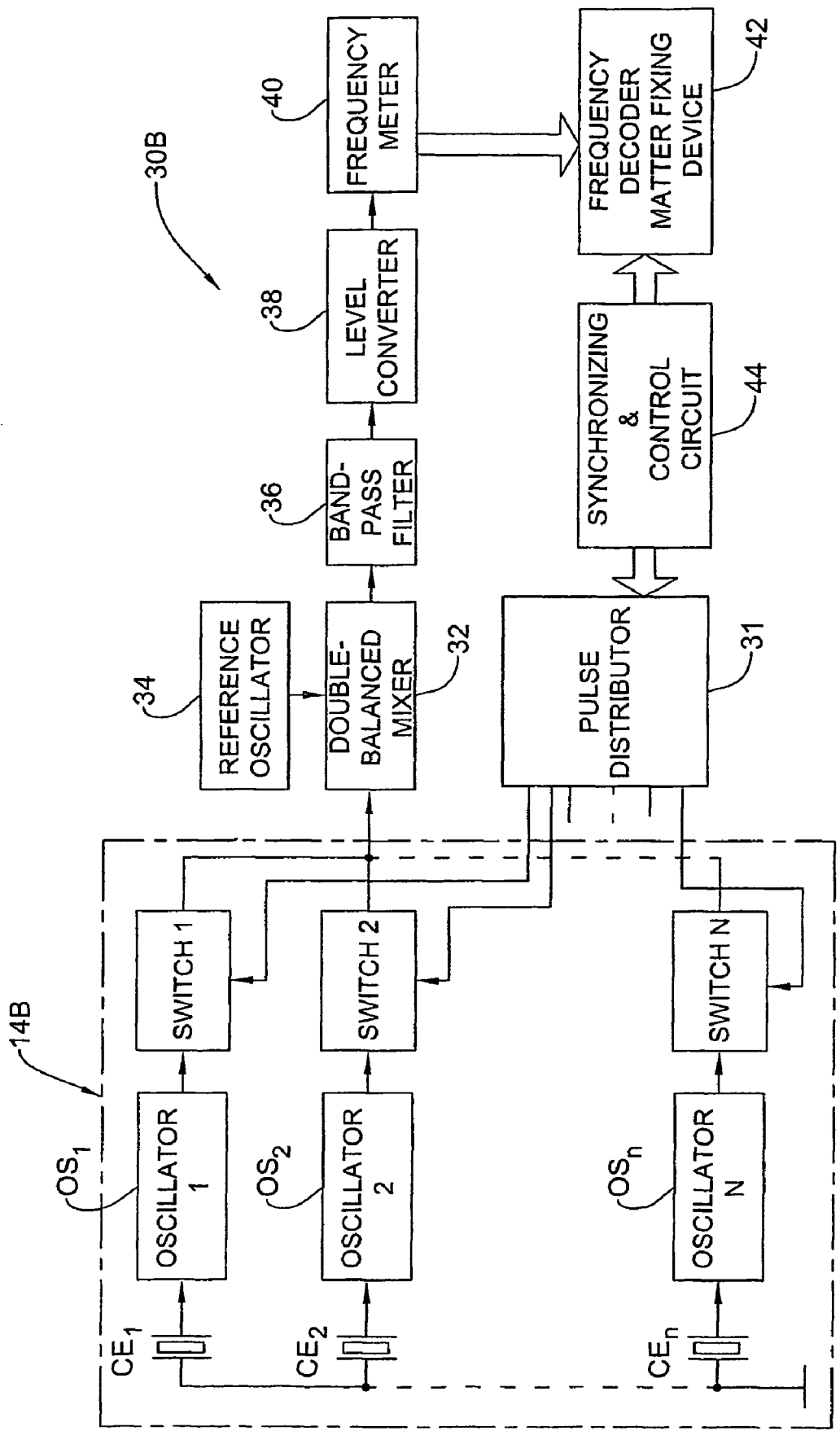

FIG. 4B illustrates a block diagram of the sensor device 10B showing the main components of the control means 30B. Similarly, to facilitate understanding, the common components in the control means 30A of FIG. 4A and 30B of FIG. 4B are identified by the same reference numbers. As shown, the control means 30B utilize the actuator utility 14B including n oscillators $OS_1$-$OS_n$ each associated with a corresponding one of the crystal resonators $CE_1$-$CE_n$.

The operation of the sensor device 10A (or 10B) is based on the creation of an electronic image of a certain foreign material and the identification of this material by means of neural network algorithms utilizing an image processing (pattern recognition) technique. The electronic image of a foreign material is created by measuring and analyzing the relative change of frequency of each quartz crystal resonator (i.e., membrane-like region) during the period of creation of the electronic image, as a combination of data generated by all quartz crystal resonators. The relative frequency change of each quartz crystal resonator corresponds to the changes of various conditions affecting the resonator. As described above, the frequency of the quartz crystal resonator is affected by the presence of a foreign material, as well as by changes in the environmental parameters. In order to reduce the effects of the environmental parameters up to a minimal value, the reference resonator $CE_1$, which is insensitive to the foreign material, is used.

The time period of the electronic image creation is defined by the synchronizing and control circuit 44. The electronic image is composed of a preset number of information packages, each package including a given number of measurement cycles. Each cycle is defined by the pulse distributor 31, by means of sequential connection of the resonators $CE_1$-$CE_n$ to the oscillator OS through the respective switches (FIG. 4A), by switching of oscillators $OS_1$-$OS_n$ via switches (FIG. 4B) or connecting the outputs of the oscillators $OS_1$-$OS_n$ to the input of the double balanced mixer 32 via respective switches (FIG. 4B).

When the quartz crystal resonator is connected to the oscillator, the latter is excited at the resonance frequency of the resonator, and the oscillator generates a corresponding signal. This signal inputs the double balanced mixer 32, which also receives a reference signal from the reference oscillator 34. The use of the mixer 32 enables to extract a signal of the relative frequency change, while keeping the parameters and the frequency changes profile unchanged, thereby enabling to reduce the measurement time and increase the accuracy of the sensor device. The band-pass filter 36 reduces the level of effects caused by the conversion up to a required value. An output signal of the filter 36 is supplied to frequency meter 40 through the level converter 38. The circuit 40 carried out frequency measurement, and a signal representative of a measured frequency value, simultaneously with information about the number of the respective quartz crystal resonator, cycle and package for the data formation supplied from the synchronizing and control circuit 44, enter the device 42. When the time of the electronic image formation expires, the information packages are mathematically processed, the foreign material is identified and an output signal indicative thereof is generated, being appropriately formatted in accordance with the user requirements.

The following table presents experimental results showing the gas sensor sensitivity of various crystal resonators characterized by different quartz crystal frequencies due to different values of the membrane thickness.

|  | Frequency (MHz) | | | | | |
| --- | --- | --- | --- | --- | --- | --- |
|  | 9 | 30 | 150 | 250 | 300 | 500 |
| Membrane Thickness (μm) | 185 | 56 | 11 | 6.7 | 5.6 | 3.3 |
| Sensitivity (g) | $1 \times 10^{-9}$ | $9.7 \times 10^{-11}$ | $1.5 \times 10^{-13}$ | $2.2 \times 10^{-14}$ | $2.4 \times 10^{-15}$ | $4.2 \times 10^{-16}$ |

The modification of the metal surface of the electrode may be achieved by two alternative techniques: (1) construction of organized, self assembled monolayers (SAM); or (2) formation of polymeric layer. These techniques are described hereinbelow:

(1) Construction of Organized SAM

The use of a piezoelectric substance such as quartz crystals covered at least partially with a metallic electrode (either gold, platinum or aluminum) provides an essential tool for the construction of organized organic monolayers. This is so due to the presence of an organized metallic layer that chemically differs from its surrounding enables the selective modification of that part with a suitable functional group. A gold or platinum electrode, for example, can be modified by sulfur containing molecules such as thiols, disulfides (either linear or cyclic) or thioethers. Aluminum electrodes can be modified by acidic moieties such as carboxylic acids and sulfonic acids.

Figure 5:
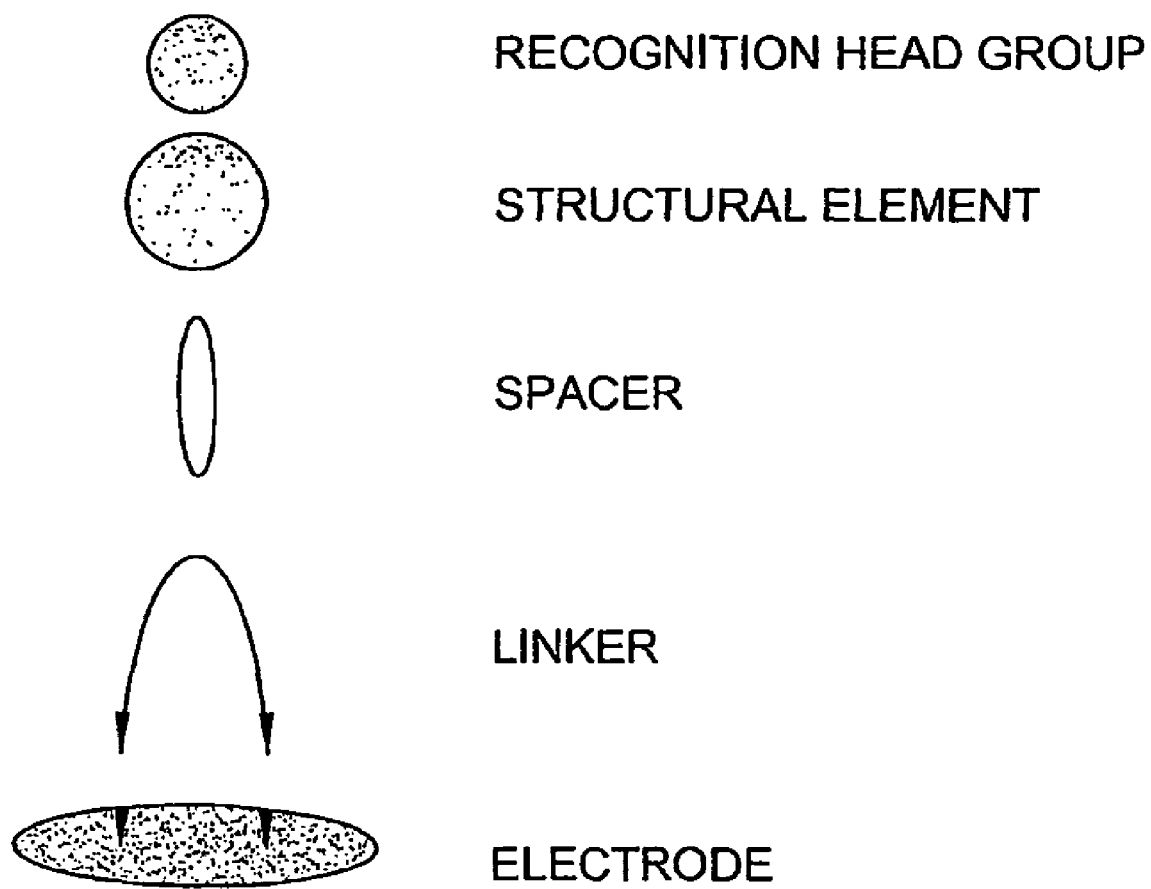
FIG. 5 schematically demonstrates the principles of modification of the metal surface of an electrode in the crystal resonator of either one of FIGS. 2A and 2B by utilizing the construction of organized, self-assembled monolayers (SAM).

The concept of SAM allows us to prepare tailor made organic molecules designed to act as artificial receptors, each binding selectively to an analyte to be detected. However, it is important to note that the artificial receptors are designed such that their interactions with an analyte are of moderate strength, leading to a reversible interaction (i.e. interaction that will enable to use the detector more than once). The artificial receptor according to the present invention comprises a linker that connects the receptor to the surface of the electrode and/or of the crystal resonator, an optional spacer, a structural element (the structural element and the optional spacer determine the 3D structure and length of the whole monolayer) and an active head group. This arrangement is schematically demonstrated in FIG. 5 for a selective receptor molecule prepared on the surface of an electrode.

Such a modular design is the basis for an unlimited arsenal of surface modifications.

The linker is the element that connects the selective receptor molecule to the surface of the electrode and/or the resonator and controls the coverage and smoothness of the monolayer. When the quartz resonators are used with a gold electrode, the linker is based on sulfur-containing compounds, for example thioethers, disulfides or thiols.

When a spacer is included in the receptor molecules, it may fulfill one or more of the following roles:
(i) To solve synthetic problems of connecting moieties that do not fit by means of functional groups. This is done by using bifunctional spacers such as bromo-acids, diamines etc.
(ii) To control the flexibility of the molecule.
(iii) To introduce some chiral discrimination when a chiral spacer is used.

The structural elements are based on molecules which promote the strong packing of the layers. Examples of such molecules are aromatic molecules, e.g. phenyl, naphthyl or larger rings, that may be optionally substituted by at least one substituent, or amino acids optionally substituted that might stabilize the monolayer through hydrogen bonds. The substituents may be of various structures, e.g. electron withdrawing or electron donating groups, depending on the characteristics of the foreign substance to be detected.

The head groups may interact with a specific foreign substance by various mechanisms, for example by forming a chemical bond or by creating a transition state resulting from weak interactions between compatible moieties, depending on the characteristics of the substance and the head group. Examples of head groups are amino, nitro, hydroxyl, thio, thiol, carboxyl and carboxyl derivatives.

Examples of chemical reactions are between functional groups such as carbazido groups and ketones to form Schiff bases (imines) or between boronic acids and diols to form boronic esters.

Except for the functional groups, the head group may also bear various substituents that affect the electron density of this element, thus altering the strength of the chemical bond or interaction between the monolayer and the substance to be detected.

Several groups of artificial receptors with varying head groups have been prepared:

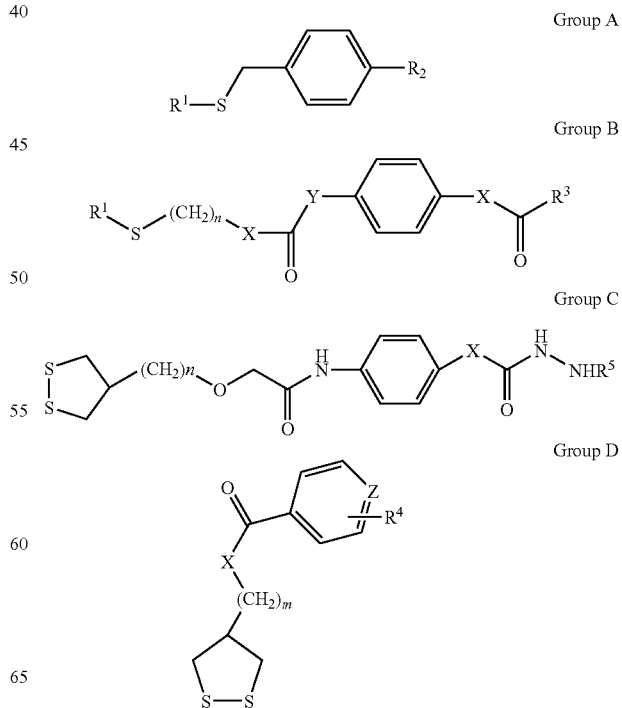

-continued
Group E
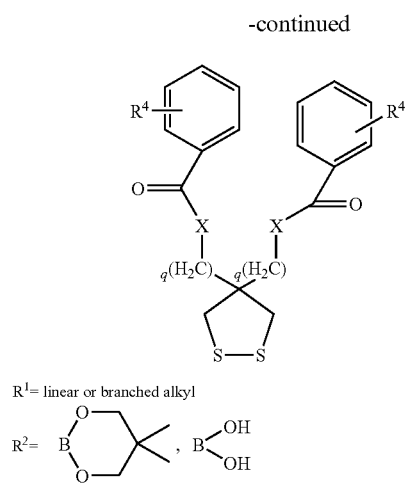
R[1]= linear or branched alkyl
R[2]=
R[3]=linear or branched alkyl or NH-NHR[5]
R[4]=H, linear or branched alkyl or alkoxy, amino, NO$_2$
R[5]=H, Boc
n=0 or an integer from 1 to 6
m-0,1,2
q=0,1,2
X=null, O or NH
Y=null, O or NH
Z=carbon or nitrogen
The following compounds are novel and constitute a further aspect of the invention:
Formula
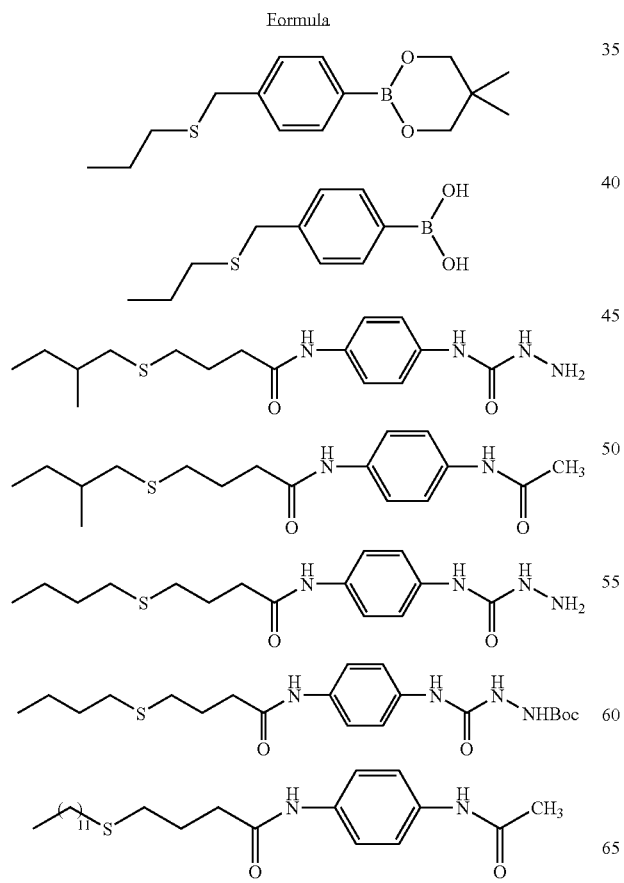
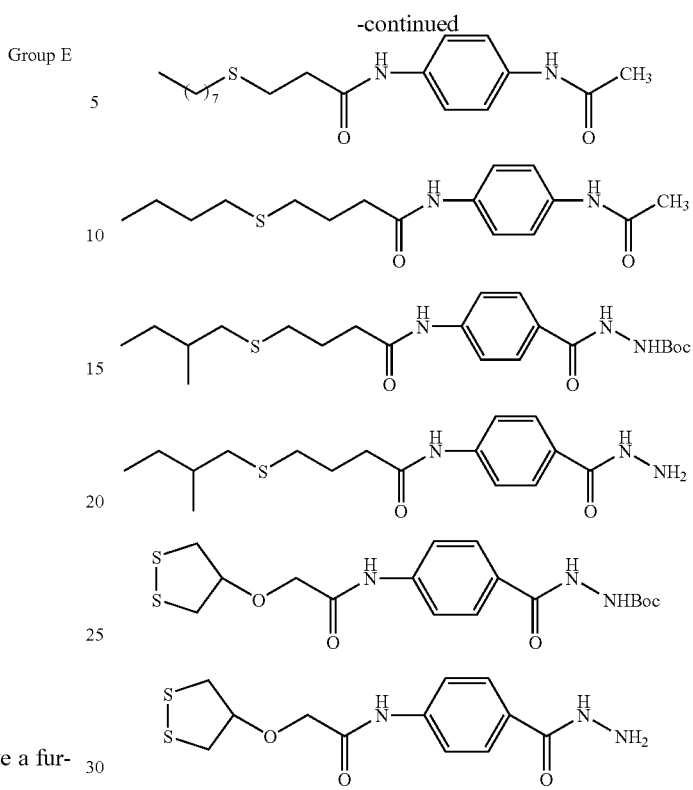
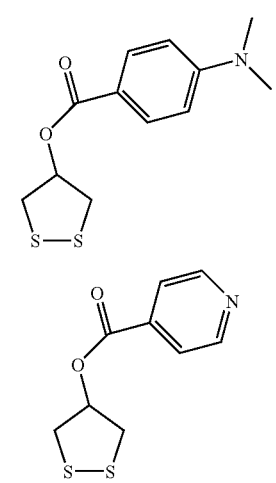

-continued

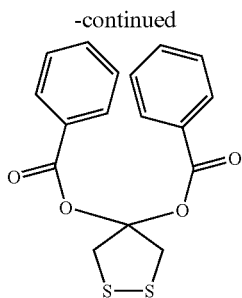

The above compounds may be prepared by know synthetic routes. For example, the compounds of Group D (when, q=0, X=O, R⁴=N(CH₃)₂) may be prepared by two alternative synthetic pathways (Method I and Method II) as follows:

Method I:

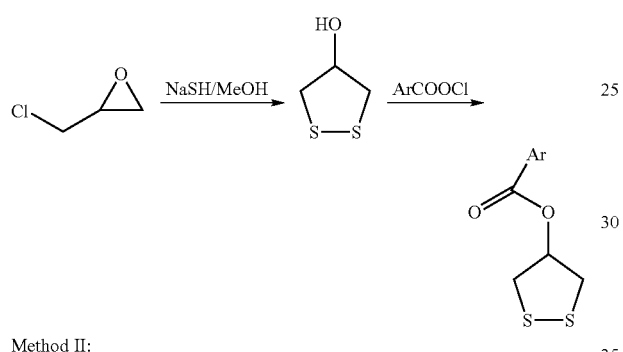

Method II:

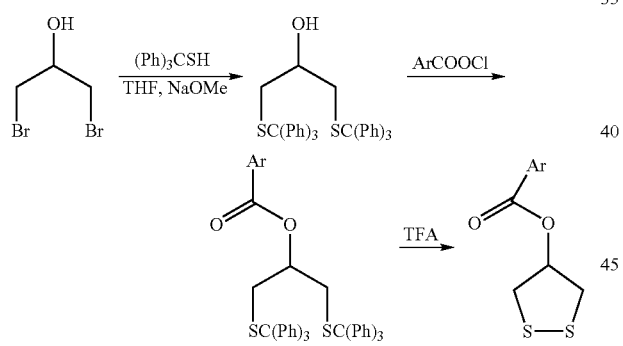

The electronic nose of the invention has potential use for the detection of hidden explosives. The chemical structures of some important explosives that are widely used by terrorists, including TATP (tiacetone triperoxide) are shown hereinbelow:

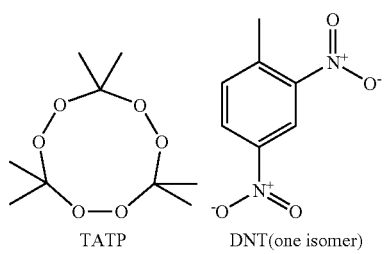

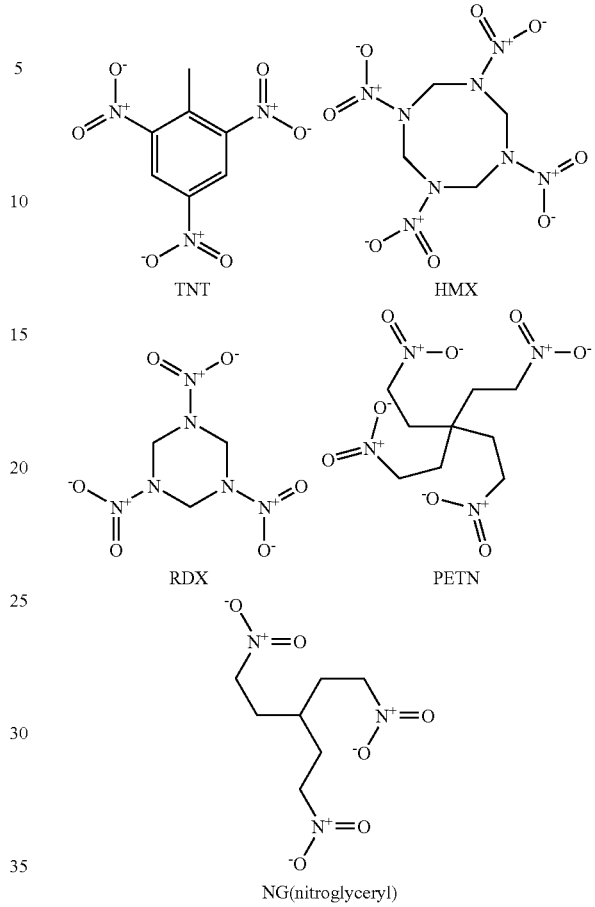

(2) Formation of Polymeric Layer

As already mentioned above, the modification of the metallic surface of the electrode can be achieved by two alternative ways, by SAM formation or by polymeric layer formation. Relating to the formation of a polymeric layer, the preferred technology for forming a polymer layer on a metallic surface in a controlled manner is by electropolymerization.

The following polymeric layers were produced and examined for adsorbing explosives: polypyrrole, polythiophene, polytriphenylene, poly(dimethylamino)pyrrole, polypyrene, polyfluorene, polyfluoranthene, polyaniline, poly(N-phenyl)aniline, poly(N-methyl)aniline and polyfluoroaniline.

The present invention is now described by the following non-limiting examples:

EXAMPLES

Example 1

General Procedure for the Preparation of a Monolayer

A quartz crystal resonator provided with a pair of gold electrodes on both surfaces thereof was treated with a solution of an sulfur molecule (0.1 mM in absolute ethanol) for 12 hours at 60° C. The resonator was then soaked for 30 min in ethanol, first at 60° C. and then at 30° C., afterwards in acetone for 20 min. at 30° C. three consequent times and dried at 60° C. for 1 hour. The thickness of the reactive monolayer formed is estimated by the change of the resonator frequency, considering also other parameters such as the electrode diameter and the quartz' density. The practically used equation for 300 MHz resonators is as follows:

$$\Delta h = \frac{-\Delta f}{-2.07 \cdot 10^{11} \rho}$$

where $\Delta h$ is the thickness of coating (Å); $\Delta f$ is the difference in frequency (Hz) (coated vs. uncoated); $\rho$ is the density of coating (g/cm$^3$), and the coefficient ($-2.07 \cdot 10^{11}$) presents the effect of the electrode diameter and the quartz' density. The value of $\rho$ is estimated to be 1.3 (according to literature).

Example 2

Preparation of Polyaniline on Quartz Resonator

A thin layer of polyaniline on quartz resonator provided with gold electrodes was prepared by two alternative methods:

1. By electropolymerization of an aqueous solution of 0.1M aniline+1M methansulfonic acid, using a potential cycling at 0-0.85V (vs. Ag/AgCl, KCl sat.) range; followed by rinsing in water and drying at 60° C.
2. By a two steps method: a) pretreatment of the resonator with an ethanolic solution of 0.001M 4-aminothiophenol for 18 hrs. at room temperature; followed by rinsing in ethanol and water, to form on the resonator surface a layer of 4-aminothiophenol; b) Electropolymerization of the product obtained in step a) in an aqueous solution of 0.1M aniline+1M methansulfonic acid, using a potential cycling at 0-0.85V (vs. Ag/AgCl, KCl sat.) range; followed by rinsing in water and drying at 60° C.

In the second method the polymerization is carried out on a preformed layer of 4-aminothiophenol in order to increase the stability of the formed polymeric layer and its uniformity.

Example 3

Synthesis of Compound (4)

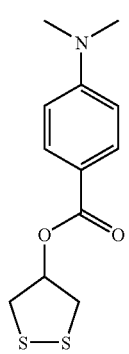

4

First Step:

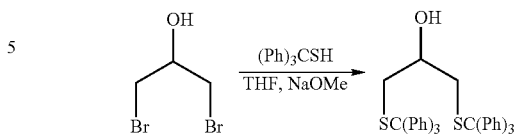

Triphenylmethanethiol (1.148 g, 0.00415 mol) was dissolved in THF (25 ml dried over basic alumina). Freshly prepared 2N NaOMe (2.3 ml) was added and the reaction mixture was stirred for half an hour. 1,3-Dibromo-2-propanol (0.19 ml, 0.0019, mol) was added and the reaction mixture was stirred for four hours at ambient temperature and then brought to reflux and heated for additional three hours. After completion of the reaction, hexane was added and the organic layer was washed with aqueous methanol (30% methanol), dried over anhydrous sodium sulfate, and concentrated. Flash chromatography with hexane:dichloromethane (6:4) as eluent afforded the product (1 g, 77%).

1H NMR (250 MHz) δ ppm: 2.1 (d, 1H, J=4 Hz, CH(OH)), 2.3 (m, 4H, CH$_2$), 3.0 (m, 1H, CH(OH)), 7.4 (m, 30H, Ar).

Second Step:

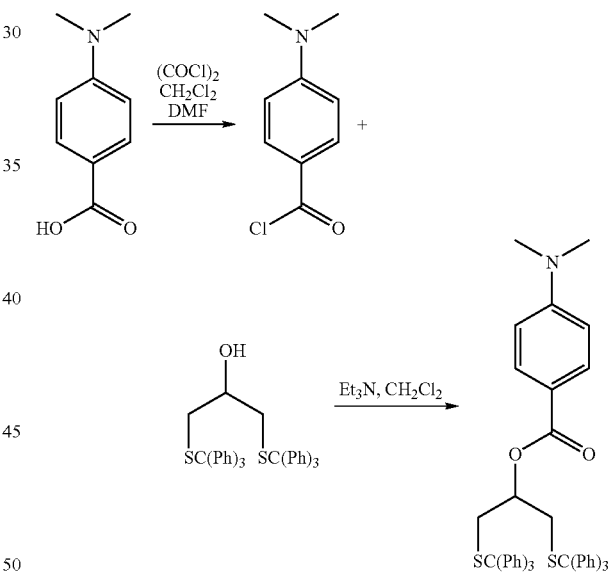

4-Dimethylamino benzoic acid (0.2 g, 0.0012 mol) was stirred with oxalyl chloride (1 ml, 0.012 mol) in dichloromethane (10 ml, dried over basic alumina) with one drop of DMF at room temperature for 4 hours. The solvent was evaporated. The residue was dissolved in dichloromethane (20 ml, dried over basic alumina) and the solution was brought to pH=8 with triethyl amine.

Basic solution of 4-dimethylaminobenzoyl chloride was added dropwise to the solution of 1,3-bis(triphenylmethanethio)-propane-2-ol (0.67 g, 0.0011 mol) in dichloromethane (10 ml, dried over basic alumina) with triethyl amine (0.2 ml, 0.0013 mol). The reaction mixture was stirred at ambient temperature for 3 hours. Hexane (100 ml) was added to the reaction mixture. Organic layer was washed with aqueous methanol (30% methanol), dried over sodium sulfate anhydrous, and concentrated. Flash chromatography with hexane:dichloromethane (6:4) afforded the product (0.7 g, 84%).

1H NMR (250 MHz) δ ppm: 2.4 (abddd, 4H, $J_1$=$J_2$=6.5 Hz, $CH_2$), 4.75 (dd, 1H, CH) 6.7 (d, 2H, J=9 Hz, Ar), 7.4 (m, 30H, 2×C(Ph)$_3$), 7.9 (d, 2H, J=9 Hz, Ar).

Third Step:

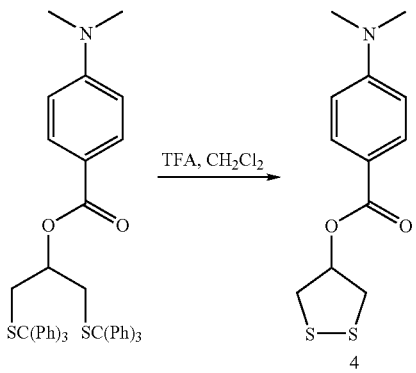

To the solution of 1,3-bis(triphenylthio)-propane-2-ol derivative (0.7 g, 0.000° mol) in dichloromethane (5 ml), trifluoroacetic acid (1 ml) was added. The reaction mixture was stirred for 4 hours at ambient temperature. The solvent was evaporated. The crude was dissolved in dichloromethane-methanol. Freshly prepared 2N sodium methylate (0.9 ml) was added followed by addition of iodine (0.47 g). Flash chromatography with hexane:ethyl acetate (6:4) afforded compound 4 (0.19 g, 78%).

1H NMR (300 MHz) δ ppm: 3.0 (s, 6H, N(CH$_3$)$_2$), 3.4 & 3.6 (abddd, 4H, $J_1$=1.8 Hz, $J_2$=8 Hz, $J_3$=62 Hz, $CH_2$), 5.8 (ddd, 1H, J=8 Hz, CH), 6.6 (d, 2H, J=9.1 Hz, Ar), 7.9 (d, 2H, J=9.1 Hz, Ar).

Example 4

Synthesis of Compound (5)

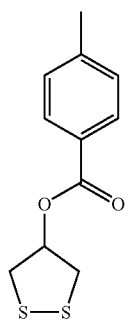

First Step:

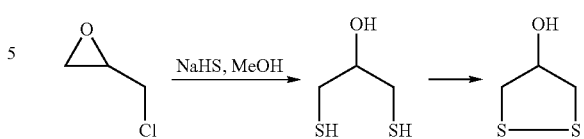

A suspension of sodium hydrogen sulfide (21 g, 0.375 mol) in methanol (150 ml) was prepared. Epichlorohydrine (5 ml, 0.065 mol) in THF (20 ml) was added dropwise at room temperature. The flask was sealed and the reaction mixture was stirred overnight at room temperature. Methanol was evaporated and the residue was dissolved in water (50 ml). Aqueous layer was extracted with chloroform. Collected organic fractions were dried over sodium sulfate and concentrated. The residue was used for further step without purification.

Second Step:

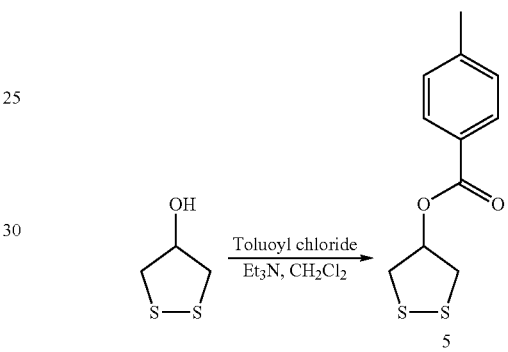

To the solution of 4-hydroxy-1,2-dithiolane (as a crude from the reaction between epichlorhydrine and sodium hydrogen sulfide) (0.1 g) in dichloromethane (dried over basic alumina 10 ml) toluoyl chloride (0.14 ml, 0.001 mol) was added followed by addition of triethylamine (0.23 ml, 0.0016 mol). The reaction mixture was stirred overnight at ambient temperature. Flash chromatography with hexane-ethyl acetate (4:6) as eluent afforded compound 5 (15 mg).

1H NMR (300 MHz) δ ppm: 2.4 (s, 3H, CH$_3$), 3.15 & 3.25 (abddd, 4H, $J_1$=3.8 Hz, $J_2$=7.2 Hz, $J_3$=15 Hz, $CH_2$), 5.8 (ddd, 1H, $J_1$=3.8 Hz, $J_2$=7.1 Hz, CH), 7.2 (d, 2H, J=8.2 Hz, Ar), 7.9 (d, 2H, J=8.2 Hz, Ar).

Example 5

Synthesis of O-benzoyl[1,2]dithiolan-4-ol (6)

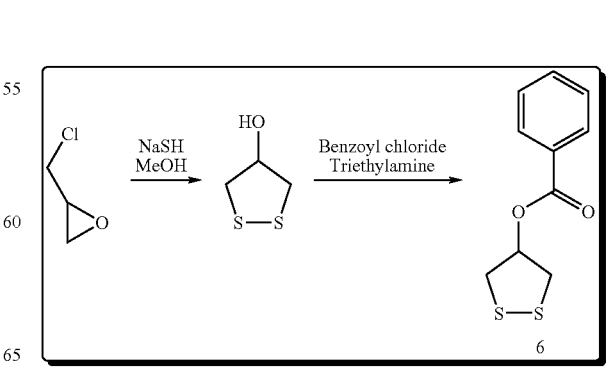

Epichlorohydrin (3 ml, 0.029 mol) was added to a solution of NASH (15 g, 0.27 mol) in MeOH (115 ml). The solution was stirred at room temperature over night. MeOH was evaporated, the residue was dissolved in brine (i.e. saturated aqueous NaCl solution), extracted several times with chloroform, dried with sodium sulfate, filtered and evaporated to dryness. The product 4-hydroxy-1,2-dithiolane was not purified for further reaction.

Benzoyl chloride (1.4 ml) and triethyl amine (1.2 ml) were added to a solution of 4-hydroxy-1,2-dithiolane (as a crude from the reaction between epichlorhydrine and sodium hydrogen sulfide) (1 gr) in dry dichloromethane (30 ml). The solution was stirred at room temperature under nitrogen over night. Dichloromethane was added to the solution, extracted several time with aqueous $K_2CO_3$ 5%, HCl 1N and Brine, dried over sodium sulfate, filtered and evaporated to dryness.

The product obtained was purified by a flash column chromatography of Silica gel with dichloromethane:hexane (2:1) as eluent to give compound 6 (0.25 gr.); NMR ($CDCl_3$, 250 MHz) δ=8.03(m, 2H, $Ar_m$), 7.58(m, 1H, $Ar_p$), 7.43(m, 2H, $Ar_o$), 5.48(m, 1H, $SCH_2CHO$), 3.21(m,4H, $SCH_2CHO$); IR ($CHCl_3$) ν=1734 $cm^{-1}$ (ester).

Example 6

Synthesis of Compound (7)

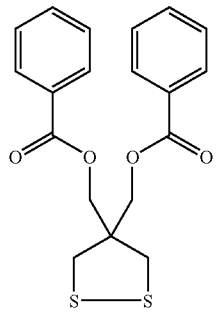

7

First Step:

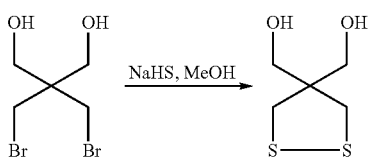

(according to the procedure in Becker H. J., Tamsma A. F, Rec. Trav. Chim, 1938, 1183-1210).

A suspension of sodium hydrogen sulfide (10.7 g, 0.19 mol) in methanol (100 ml) was prepared. 2,2-Bis(bromomethyl)-1,3-propanediol (5 g, 0.019 mol) in methanol (20 ml) was added dropwise at room temperature. The flask was sealed and the reaction mixture was stirred for 18 hours at room temperature and then refluxed for 2 additional hours. One third of methanol was evaporated and ethyl acetate was added (50 ml). The precipitate was filtered out and the procedure was repeated four times with supernatant. Ethyl acetate was evaporated. Recrystallization from hot toluene afforded the product (1.6 g; 50%).

1H NMR (250 MHz, $CD_3OD$) δ ppm: 2.9 (s, 2H, $CH_2S$), 3.6 (s, 2H, $CH_2O$).

Second Step:

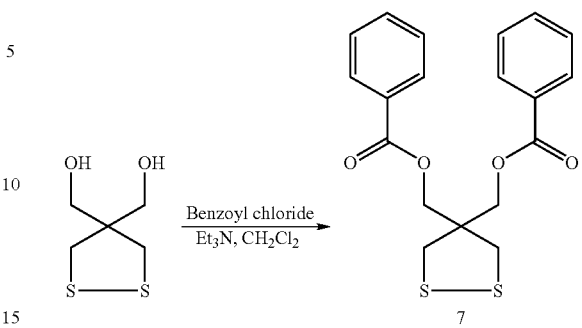

To the solution of 4,4-bis(hydroxymethyl)-1,2-dithiolane (0.15 g, 0.0009 mol) in dichloromethane (dried over basic alumina 10 ml) benzoyl chloride (0.23 ml, 0.002 mol) was added followed by addition of triethylamine (0.29 ml, 0.002 mol). The reaction mixture was stirred overnight at ambient temperature. Flash chromatography with hexane-chloroform (6:4) as eluent afforded the product (120 mg, 35%).

1H NMR (300 MHz, $CDCl_3$) δ ppm: 3.2 (s, 2H, $CH_2S$), 4.5 (s, 2H, $CH_2O$), 7.4 (dd, 2H, $J_1=J_2=7.8$ Hz, Ar), 7.55 (dd, 1H, $J_1=J_2=7.8$ Hz, Ar), 8.0 (d, 2H, J=7.8 Hz).

Example 7

Synthesis of Thioether Carbazido Compound (8)

The compound was synthesized via the following pathway:

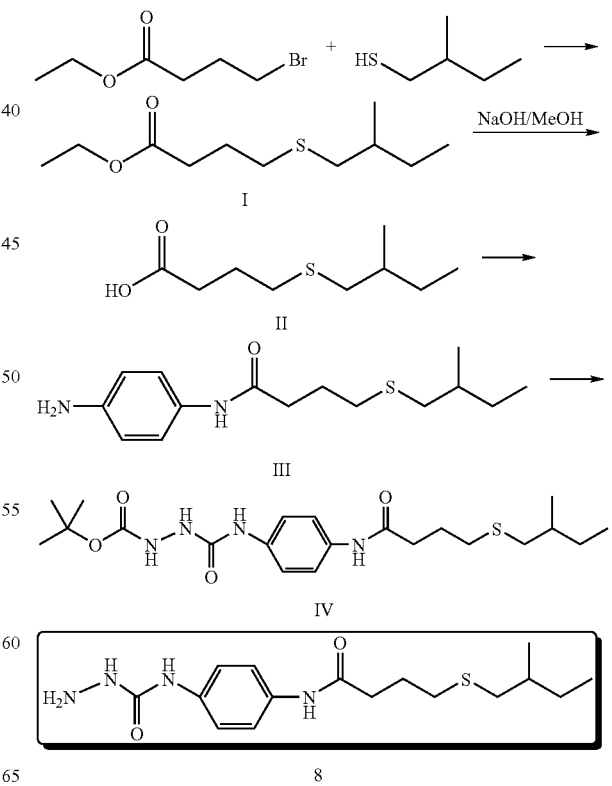

First Step: Synthesis of I:

Anhydrous potassium carbonate was added to a solution of 2-methyl-1-butanethiol in DMF. Bromo-ethylbutyrate was added and stirred over night.

The solution was dissolved in a mixture of hexane/ethyl acetate (1:3) and washed several times with water, dried over $Na_2SO_4$, filtered and evaporated to dryness. The product I may contain traces of the thiol.

Second Step: Synthesis of II:

The ester I was dissolved in MeOH (10 ml/mmol) and 1N NaOH (1.1 ml) and stirred for 1 hour. In a case that the reaction was not ended, additional aliquot of NaOH was added. After the consumption of the ester, MeOH was evaporated, the residue was dissolved in water and washed with EtOAc. The basic aqueous solution was acidified with $KHSO_4$ 1M to pH 4. The product was extracted several times with EtOAc, dried over $Na_2SO_4$, filtered and evaporated to dryness. The overall yield of the two steps is close to quantitative.

NMR ($CDCl_3$, 250 MHz) δ=2.5 (m, 6H, three methylene groups), 1.85 (m, 2H, $SCH_2CH_2CH_2$), 1.47 (m, 2H, $CH_3CH_2CH(CH_3)$), 1.18 (m, 1H, $CH_3CH_2CH(CH_3)$), 0.94 (d, J=6.5H, 3H, $CH_3CH_2CH(CH_3)$), 0.87(d, J=7 Hz, 3H, $CH_3CH_2CH(CH_3)$). IR ($CHCl_3$) ν=1715 $cm^{-1}$ (COOH).

Third Step: Synthesis of III:

Oxalyl chloride (4.5 ml) and a few drops of DMF were added to a solution of the acid II (1.6 gr.) in dry dichloromethane and kept under inert atmosphere over night. The solvents were removed in vacuo, the residue was dissolved in dry dichloromethane and introduced in a dropping funnel under nitrogen stream. The acyl chloride was added dropwise to a solution of p-phenylene diamine in DMF (3.5 ml in 15 ml DMF) and the mixture was stirred for two hours. Chloroform was added and the organic solution was washed with water and dried. The product was purified by flash column chromatography (chloroform:MeOH 95:5 as eluent) to give pure product. (900 mg, 40%).

NMR ($CDCl_3$, 250 MHz) δ=7.5(b, 1H, CONHAr), 7.25+6.6 (Abq, 4H,Ar) 2.5 (m, 6H, three methylene groups), 1.95 (m, 2H, $SCH_2CH_2CH_2$), 1.5 (m, 2H, $CH_3CH_2CH(CH_3)$), 1.2 (m, 1H, $CH_3CH_2CH(CH_3)$), 0.94 (d, J=6.5 Hz, 3H, $CH_3CH_2CH(CH_3)$), 0.87(d, J=7 Hz, 3H, $CH_3CH_2CH(CH_3)$). IR ($CHCl_3$) ν=1670 $cm^{-1}$ (CONH).

Fourth Step: Synthesis of IV:

Triphosgene (400 mg.) and 2,6 lutidine (1 ml) were added to a solution of the free amine III (900 mg) in dry dichloromethane under inert atmosphere and stirred for 10 min. t-Bu-carbazate (500 mg) was added and the mixture was left for an hour. Chloroform was added and the organic solution was washed with $NaHCO_3$ 1N, HCl 1N, water and dried. The product was purified by flash column chromatography (chloroform:MeOH 95:5 as eluent) to give 700 mg almost pure product IV. The product was recrystallized from MeOH/ether to give of pure IV (500 mg., 35%). NMR ($CDCl_3$, 250 MHz) δ=8.27 (b, 1H, NHNHBoc), 7.79 (b, 1H, NHNHBoc), 7.4 (b, 1H, CONHAr), 7.7 (m, 4H,Ar), 2.5 (m, 6H, three methylene groups), 1.98 (m, 2H, $SCH_2CH_2CH_2$), 1.5 (m, 1H, Boc+ $CH_3CH_2CH(CH_3)$), 1.2 (m, 1H, $CH_3CH_2CH(CH_3)$), 0.97 (d, J=6.5 Hz, 3H, $CH_3CH_2CH(CH_3)$), 0.88(d, J=7 Hz, 3H, $CH_3CH_2CH(CH_3)$). IR ($CHCl_3$)) ν=1670 $cm^{-1}$ (CONH), 1710 $cm^{-1}$ (Boc).

Last Step: Synthesis of 8:

The boc-protected semicarbazide IV (160 mg.) prepared above was treated with 15% TFA in dichloromethane over night, the solvent was removed, the residue was treated with triethylamine (in methanol) to obtain neutral pH, dried, and purified by flash column chromatography (chloroform: MeOH 95:5 as eluent) to give of product 8. (100 mg, 80%).

NMR (MeOD+$CDCl_3$, 250 MHz) δ=7.4 (m, 4H,Ar), 2.45 (m, 6H, three methylene groups), 1.92 (m, 2H, $SCH_2CH_2CH_2$), 1.4 (m, 2H, $CH_3CH_2CH(CH_3)$), 1.1 (m, 1H, $CH_3CH_2CH(CH_3)$), 0.89 (d, J=6.5 Hz, 3H, $CH_3CH_2CH(CH_3)$), 0.83 (d, J=7 Hz, 3H, $CH_3CH_2CH(CH_3)$).

Example 8

Synthesis of Acetanilide Derivatives 9 and 10

The acetanilide derivatives 9 and 10 were synthesized in a three-step procedure, as showed below:

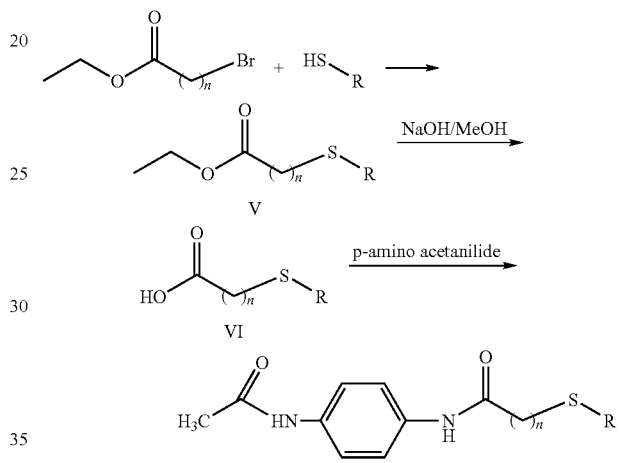

Compound 9: R=$(CH_2)_7CH_3$, n=2

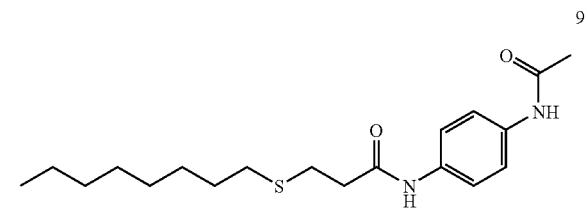

The first two steps are identical to those of the synthesis of compound 8. Oxalyl chloride (5 ml) and a few drops of DMF were added to a solution of the acid VI (0.8 gr.) in dry dichloromethane and kept under inert atmosphere over night. The solvents were removed in vacuo, the residue was dissolved in dry dichloromethane. p-Amino acetanilide (0.8 gr.) and triethylamine (1 ml) were added to the solution and stirred at room temperature for additional 3 hours. The solution was washed with HCl 1N and aqueous $K_2CO_3$ (5%), dried over $MgSO_4$ followed by column purification (chloroform:ethyl acetate 1:1 as eluent) to provide pure compound 9. (400 mg., 31%)

NMR ($CDCl_3$, 250 MHz) δ=7.58 (b, 1H, NH), 7.45 (s, 4H, Ar), 7.17 (b, 1H, NH), 2.89 (t, J=7 Hz, 2H, $CH_2CO$) 2.56 (m, 4H, $CH_2SCH_2$), 2.17 (s, 3H, $COCH_3$), 1.25 (m, 12H, $CH_3(CH_2)_6CH_2$), 0.87 (bt, 3H, $CH_3(CH_2)_6CH_2$).

Synthesis of Compound (10): R=(CH$_2$)$_3$CH$_3$, n=3

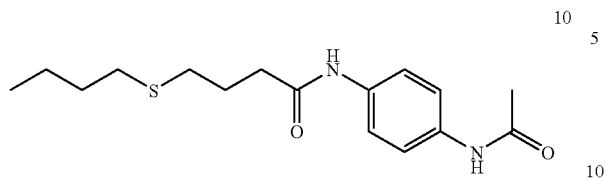

The first two steps are identical to those of the synthesis of compound 8. Oxalyl chloride (10 ml) and a few drops of DMF were added to a solution of the acid VI (2.6 gr.) in dry dichloromethane and kept under inert atmosphere over night. The solvents were removed in vacuo, the residue was dissolved in dry dichloromethane. p-Amino acetanilide (2 gr.) and triethylamine (2 ml) were added to the solution and stirred at room temperature for additional 3 hour. The solution was washed with HCl 1N and aqueous K$_2$CO$_3$ (5%), dried over MgSO$_4$ followed by column purification (methylene chloride:ethyl acetate 1:1 as eluent) to provide pure compound 10. (800 mg., 18%)

NMR (CDCl$_3$, 250 MHz) δ=7.46 (s, 4H,Ar), 7.25 (b, 1H, NH), 7.15 (b, 1H, NH), 2.60 (t, J=7 Hz, 2H, CH$_2$CO) 2.5 (m, 4H, CH$_2$SCH$_2$), 2.17 (s,3H, COCH$_3$), 2.05 (m, 2H, CH$_2$CH$_2$CO), 1.42 (m, 4H, CH$_3$(CH$_2$)$_2$CH$_2$), 0.91 (t, J=7 Hz, 3H, CH$_3$(CH$_2$)$_2$CH$_2$).

Example 9

Affinity and Selectivity Experiments

The following receptor molecules have been tested:

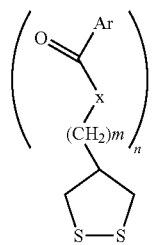

Compound 4 m = 0, n = 1, Ar = [phenyl-N(CH$_3$)$_2$]

Compound 5 m = 0, n = 1, Ar = [phenyl-CH$_3$]

Compound 6 m = 0, n = 1, Ar = [phenyl]

Compound 7 m = 1, n = 2, Ar = [phenyl]

-continued

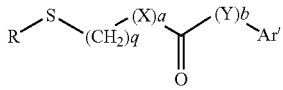

Compound 8 R-isopentyl; Y = NH; a = 0, b = 1; q = 3;

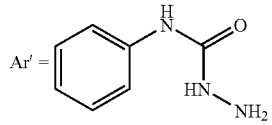

Compound 9 R = n-octyl; Y = NH; a = 0, b = 1; q = 2;

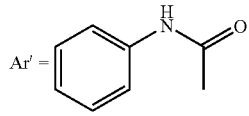

Compound 10 R = n-butyl; Y = NH; a = 0, b = 1; q = 3;

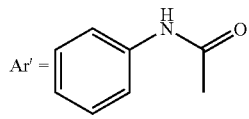

The affinity and selectivity of the receptors 4-10 and of a few polymeric receptors were examined in the following way:

i—A 250 MHz quartz crystal resonator was first modified with a monolayer comprising one of the artificial receptors 4-10.

ii—Three analytes were checked: TATP, Naphthalene and 2,3-dimethyl-2,3-dinitrobutane, each having a specific vapor pressure.

iii—The frequency change of the resonator due to the exposure to the vapor of ~100 μg of the analyte at room temperature in a 2 cc chamber was recorded within 60 sec.

The following table summarizes the maximum response (measured in Hz) of some modified resonators to the tested analytes:

| Compound | TATP | Naphthalene | DDB |
|---|---|---|---|
| 4 | 1370 | 2500 | 380 |
| 5 | 720 | 700 | 230 |
| 6 | 6950 | 1900 | 250 |
| 7 | 4750 | 2520 | 300 |
| 8 | 300 | 1000 | 80 |
| 9 | 650 | 1080 | 230 |
| 10 | 4200 | 1350 | 780 |
| Polyfluorene | 1100 | 2100 | 420 |
| Polypyrrole | 1500 | 2900 | 320 |
| Poly (N-methyl aniline) | 1300 | 1950 | 130 |

Example 10

Detection of Iohexole in Liquid Environment

The boronic acid derivative 11 synthesized for the detection of iohexole in solution has the following structure:

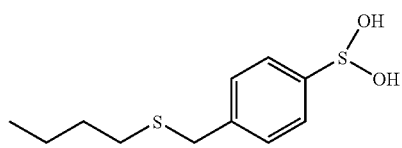

Iohexole is a compound used as a source for iodine needed for CT scans. However, the secretion of iohexole in the urine may also indicate certain gastro diseases.

IOHEXOLE

The boronic acid derivative was prepared according to the following scheme:

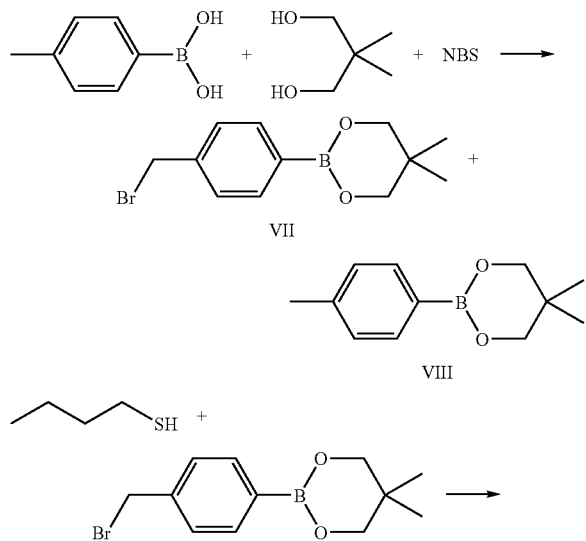

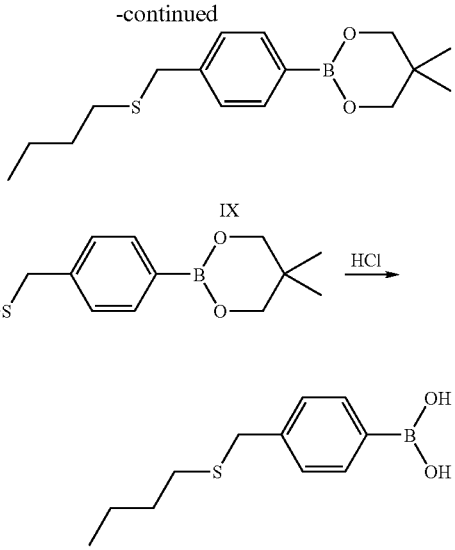

a) Synthesis of p-Bromomethyl Phenyl Boronic Acid-Neopentyl Ester (VII and VIII)

(according to the procedure in Nakao H. et al. Biosci. Biotech. Biochem. 60(4) 1996, 683-684.)

p-Toluene boronic acid (750 mg.) and neopentyl glycol (600 mg.) were dissolved in 50 ml cyclohexane and heated at reflux for 1.5 hours. N-Bromosuccinimide (1.15 g.), benzoyl peroxide (25 mg.) and 150 ml cyclohexane were added and the solution was heated at reflux for additional 2 hours. The solution was cooled to room temperature, filtered and evaporated to give a mixture of VII and VIII (total of 1.3 g, ~1:1 ratio), the yield=47%.

NMR (CDCl$_3$, 250 MHz) δ=7.81+7.38 (Abq, 4H,Ar), 5.50 (s, 2H, ArCH$_2$Br), 3.77 (s, 4H, OCH$_2$C), 1.03 (s, 6H, C(CH$_3$)$_2$).

b) Synthesis of IX:

Anhydrous potassium carbonate was added to a solution of 1-butanethiol (90 μl) in DMF. A (450 mg.) was added and the mixture was stirred over night.

The solution was dissolved in a mixture of hexane/ethyl acetate (1:3) and washed several times with water, dried over Na$_2$SO$_4$, filtered and evaporated to dryness. The product was purified by flash column chromatography (ethyl acetate: dichloromethane 4:6 as eluent). Yield=15%.

NMR (CDCl$_3$, 250 MHz) δ=7.72+7.27 (Abq, 4H,Ar), 3.74 (s, 4H, OCH$_2$C), 3.68 (s,2H, ArCH$_2$S) 2.40 (m, 2H, SCH$_2$CH$_2$CH$_2$CH$_3$), 1.54 (m, 2H, SCH$_2$CH$_2$CH$_2$CH$_3$), 1.31 (m, 2H, SCH$_2$CH$_2$CH$_2$CH$_3$), (m1.00 (s, 6H, C(CH$_3$)$_2$), 0.85 (t, J=7 Hz, 3H, SCH$_2$CH$_2$CH$_2$CH$_3$).

c) Synthesis of 11

The boronic ester IX (50 mg.) was hydrolyzed in THF/HCl 2N (1:1) over night at room temperature. The THF was evaporated, the residue was dissolved in ethyl acetate, washed with water and purified by three consequence chromatography columns ((i) CHCl$_3$:MeOH 97:3, (ii) CHCl$_3$:MeOH 99:1, n-Hexane:Ethyl acetate (gradient from 20% to 50% ethyl acetate)). Yield=15%.

NMR (CDCl$_3$, 250 MHz) δ=7.20+6.73 (Abq, 4H,Ar), 3.65 (s,2H, ArCH$_2$S) 2.43 (m, 2H, SCH$_2$CH$_2$CH$_2$CH$_3$), 1.28 (m, 4H, SCH$_2$CH$_2$CH$_2$CH$_3$), 0.88 (t, J=7 Hz, 3H, SCH$_2$CH$_2$CH$_2$CH$_3$).

Measurements were performed with 30 MHz resonators in water. The response of a resonator coated with the boronic acid derivative 11, in distilled water, was compared to that of a 25 μg/ml solution of iohexole as an analyte.

The response of the resonator to the iohexole solution was in the range of 600 Hz.

Those skilled in the art will readily appreciate that various modification and changes can be applied to the embodiments of the invention as hereinbefore described and exemplified without departing from its scope defined in and by appended claims.

The invention claimed is;

1. An organized, self-assembled monolayer (SAM) on a sensing surface of a sensor device for identifying at least one foreign material from environment, said monolayer consisting of the receptor compound of Formula A below wherein q=0, X=O, R$^4$=H, linear or branched alkyl or alkoxy, amino or NO$_2$ group and Z=C or N, said receptor compound being configured for binding selectively to an analyte to be detected through hydrogen bonds.

Formula A:

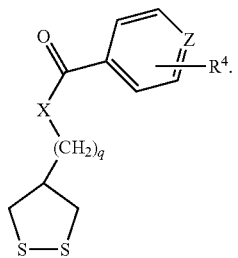

2. The SAM according to claim 1, wherein said sensing surface is a surface of at least one of the following: an Au electrode, and a crystal's surface of a piezoelectric crystal resonator.

3. The SAM according to claim 2, wherein said sensing surface is made of Au.

4. The SAM according to claim 1, wherein said R$^4$ is N(CH$_3$)$_2$.

* * * * *